US009750445B2

United States Patent
Liu et al.

(10) Patent No.: US 9,750,445 B2
(45) Date of Patent: Sep. 5, 2017

(54) POROUS POLYMERIC FORMULATION PREPARED USING POROGENS

(71) Applicant: Verily Life Sciences LLC, Mountain View, CA (US)

(72) Inventors: Zenghe Liu, Mountain View, CA (US); Jeffrey George Linhardt, Mountain View, CA (US); Huanfen Yao, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 858 days.

(21) Appl. No.: 13/930,877

(22) Filed: Jun. 28, 2013

(65) Prior Publication Data

US 2015/0005603 A1 Jan. 1, 2015

(51) Int. Cl.
*A61B 5/1486* (2006.01)
*A61B 5/145* (2006.01)
*A61B 5/00* (2006.01)

(52) U.S. Cl.
CPC ........ *A61B 5/1486* (2013.01); *A61B 5/14532* (2013.01); *A61B 5/14507* (2013.01); *A61B 5/14546* (2013.01); *A61B 5/682* (2013.01); *A61B 5/6821* (2013.01)

(58) Field of Classification Search
CPC ............. G01N 27/3274; G01N 27/327; G01N 27/3272; A61L 2/206; A61B 5/14532; A61B 5/14546; A61B 5/1486
See application file for complete search history.

(56) References Cited

U.S. PATENT DOCUMENTS

| 4,929,313 | A | 5/1990 | Wrighton |
| 5,543,326 | A | 8/1996 | Heller et al. |
| 5,683,563 | A * | 11/1997 | Mizutani ............... C12Q 1/002 |
| | | | 204/403.1 |
| 5,928,918 | A | 7/1999 | Offenbacher |
| 6,653,358 | B2 | 11/2003 | Bruza |
| 6,654,625 | B1 | 11/2003 | Say et al. |

(Continued)

FOREIGN PATENT DOCUMENTS

| EP | 1927602 | 6/2008 |
| WO | 2012115501 | 8/2012 |
| WO | 2012161735 | 11/2012 |

OTHER PUBLICATIONS

International Search Report issued in connection with co-pending International Patent Application No. PCT/US2014/044611, ISA/KR dated Oct. 15, 2014, 6 pgs.

(Continued)

*Primary Examiner* — Gurpreet Kaur
(74) *Attorney, Agent, or Firm* — McDonnell Boehnen Hulbert & Berghoff

(57) ABSTRACT

An analyte sensor for the continuous or semi-continuous monitoring of physiological parameters and a method for making the analyte sensor are disclosed. The analyte sensor includes a crosslinked copolymer network in contact with a surface of an electrode. The copolymer network has voids formed by the removal of a porogen, and an analyte sensing component is immobilized within the network. The method involves forming a solution of the precursors of the copolymer, depositing the mixture on a surface of an electrode, and curing the deposited mixture to provide the analyte sensor.

11 Claims, 1 Drawing Sheet

(56) References Cited

U.S. PATENT DOCUMENTS

| | | |
|---|---|---|
| 6,927,246 B2 | 8/2005 | Noronha |
| 7,731,835 B2 | 6/2010 | Buck |
| 7,959,791 B2 | 6/2011 | Kjaer |
| 8,088,595 B2 | 1/2012 | Ibey |
| 8,224,414 B2 | 7/2012 | Kellogg |
| 8,241,819 B2 | 8/2012 | Lowe |
| 8,385,998 B2 | 2/2013 | Zhang |
| 8,437,829 B2 | 5/2013 | Mao |
| 2004/0256227 A1 | 12/2004 | Shin |
| 2007/0114138 A1 | 5/2007 | Krasteva et al. |
| 2008/0281178 A1 | 11/2008 | Chuang |
| 2009/0280181 A1 | 11/2009 | Slager |
| 2010/0175992 A1 | 7/2010 | Shah |
| 2010/0279377 A1 | 11/2010 | Shah |
| 2010/0280347 A1 | 11/2010 | Shah |
| 2010/0300897 A1 | 12/2010 | Savage |
| 2011/0082356 A1 | 4/2011 | Yang et al. |
| 2011/0136929 A1 | 6/2011 | Chow |
| 2011/0152654 A1 | 6/2011 | Wang |
| 2012/0116191 A1 | 5/2012 | Markle |
| 2012/0186997 A1* | 7/2012 | Li .................. C12Q 1/00 205/778 |
| 2012/0201755 A1 | 8/2012 | Rozakis |
| 2012/0245444 A1 | 9/2012 | Otis |
| 2012/0283537 A1 | 11/2012 | Petisce |
| 2012/0296186 A1 | 11/2012 | Ouyang et al. |
| 2013/0011460 A1 | 1/2013 | Liu |
| 2013/0084649 A1 | 4/2013 | Crane |

OTHER PUBLICATIONS

Written Opinion issued in connection with co-pending International Patent Application No. PCT/US2014/044611, ISA/KR dated Oct. 15, 2014, 8 pgs.

Gil, M.H., et al., "Immobilization of Glucose Oxidase on Thin-Film Gold Electrodes Produced by Magnetron Sputtering and Their Application in an Electrochemical Biosensor," Biotechnology Techniques, vol. 13, pp. 595-599 (1999).

Hall, C.E. et al., "Covalent Immobilisation of Glucose Oxidase on Methacrylate Copolymers for Use in an Amperometric Glucose Sensor," Analytica Chimica Acta, vol. 281, pp. 645-653 (1993).

Jusoh, Norhana et al., "Improvement of Glucose Biosensor Performances Using Poly(hydroxyethylmethacrylate) Outer Membrane," International Journal of Biology and Biomedical Engineering, Issue 1, vol. 6, pp. 77-86 (2012).

Slaughter, Gymama Ph.D., "Fabrication of Nanoindented Electrodes for Glucose Detection," Journal of Diabetes Science and Technology, vol. 4, Issue 2, pp. 320-327 (Mar. 2010).

Akkaya, et al., "Functional polymer supports for immobilization of cholesterol oxidase," Biochemical Engineering Journal, vol. 43, No. 3, Mar. 2009, p. 333-337.

* cited by examiner

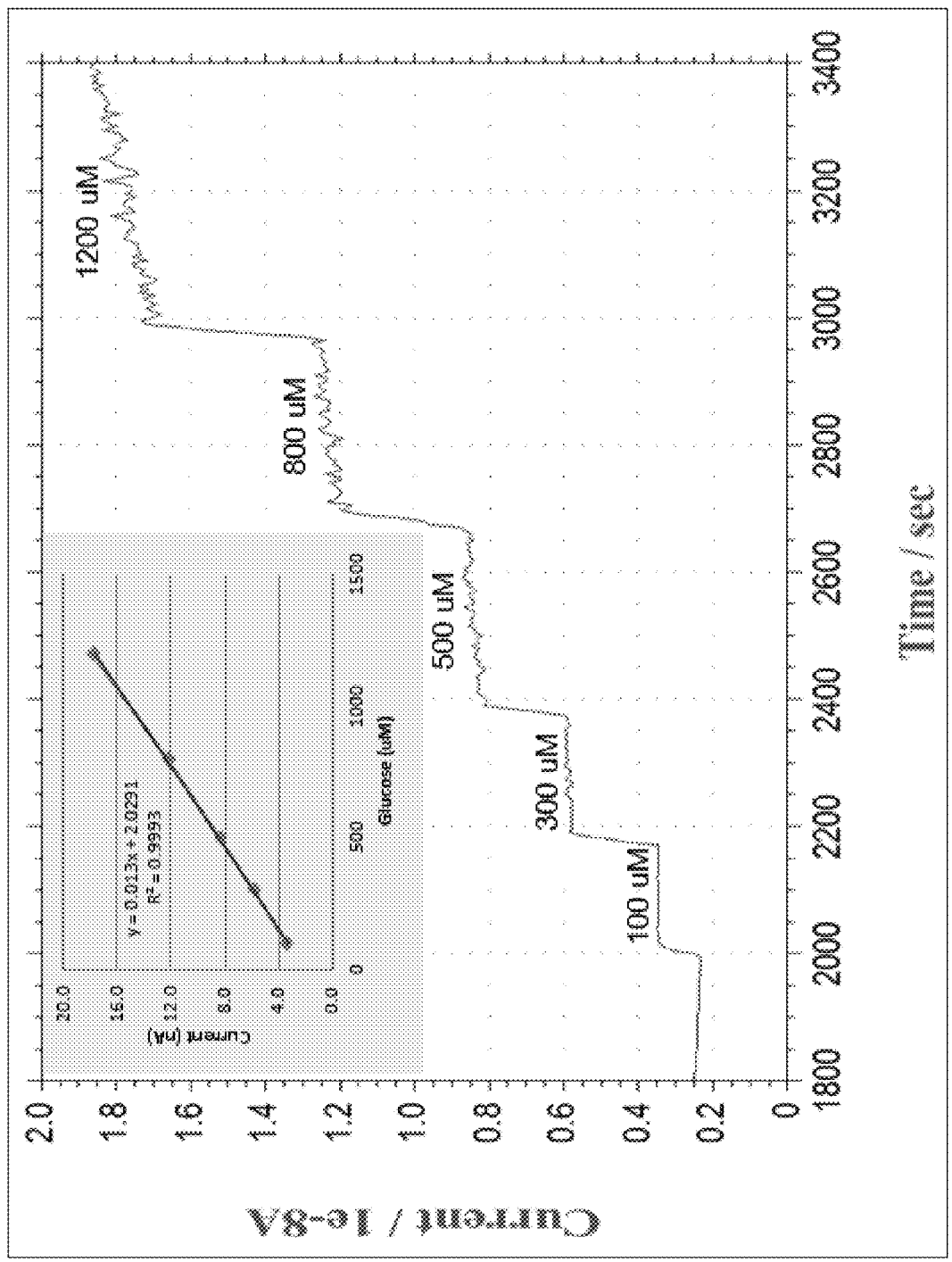

POROUS POLYMERIC FORMULATION PREPARED USING POROGENS

BACKGROUND

Unless otherwise indicated herein, the materials described in this section are not prior art to the claims in this application and are not admitted to be prior art by inclusion in this section.

The continuous or semi-continuous monitoring of physiological parameters has applications in many areas of modern medicine. Electrochemical-based sensors are believed to be particularly suitable for the monitoring and quantification of analytes (e.g., glucose) in bodily fluid samples (e.g., blood, tear film, urine or interstitial fluid samples). The use of an electrochemical-based sensor that employs an analyte sensing component, (e.g., an enzyme) in conjunction with an electrode(s) allows for the quantification of an analyte in a liquid sample by detecting the product(s) produced from the reaction of the analyte sensing component and the analyte.

SUMMARY

In one aspect, an analyte sensor is disclosed. The analyte sensor includes a crosslinked polymer network in contact with a surface of an electrode, and an analyte sensing component immobilized within the network. The polymer network includes backbone chains having first methacrylate-derived units and second methacrylate-derived units. Each first methacrylate-derived unit has a side chain, and the second methacrylate-derived units in different backbone chains are connected by crosslinks. The crosslinked polymer has voids, or pores, within and defined by the network.

In another aspect, a method for forming an analyte sensor is disclosed. The method involves forming a solution including an analyte sensing component, one or more porogens, a dimethacrylate monomer, an initiator, and a methacrylate monomer having a side chain, depositing the mixture on a surface of an electrode, and curing the deposited mixture to provide the analyte sensor.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 1 is a graph of current produced by an example glucose sensor at glucose concentrations of 100 µM to 1,200 µM in phosphate buffered saline (PBS). A linear relationship between current and glucose concentration was observed (see inset graph).

DETAILED DESCRIPTION

The following detailed description describes various features and functions of the disclosed systems and methods with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and in a wide variety of different configurations, all of which are contemplated herein.

In one aspect, an analyte sensor is disclosed. The analyte sensor includes a crosslinked copolymer network in contact with a surface of an electrode, where the network includes:
backbone chains including first methacrylate-derived units and second methacrylate-derived units, where each first methacrylate-derived unit has a side chain;
crosslinks between the second methacrylate-derived units in different backbone chains;
an analyte sensing component embedded within the network; and
voids within and defined by the copolymer network.

In some embodiments, the analyte sensor can be an enzyme-based biosensor. These devices are able to convert an analyte-concentration-dependent biochemical reaction signal into a measurable physical signal, such as an optical or electrical signal. The biosensors can be used in the detection of analytes in clinical, environmental, agricultural and biotechnological applications. Analytes that can be measured in clinical assays of fluids of the human body include, for example, glucose, lactate, cholesterol, bilirubin and proteins, lipids and electrolytes. The detection of analytes in biological fluids, such as blood, tear film, or intestinal fluid, can be important in the diagnosis and the monitoring of many diseases.

In some embodiments, the analyte sensor can be a component of a body-mountable device, such as an eye-mountable, tooth-mountable, or skin-mountable device. The eye-mountable device can be configured to monitor health-related information based on one or more analytes detected in a tear film (the term "tear film" is used herein interchangeably with "tears" and "tear fluid") of a user wearing the eye-mountable device. For example, the eye-mountable device can be in the form of a contact lens that includes a sensor configured to detect one or more analytes (e.g., glucose). The eye-mountable device can also be configured to monitor various other types of health-related information.

In some embodiments, the body-mountable device may comprise a tooth-mountable device. The tooth-mountable device may take the form of or be similar in form to the eye-mountable device, and be configured to detect at least one analyte in a fluid (e.g., saliva) of a user wearing the tooth-mountable device.

In some embodiments, the body-mountable device may comprise a skin-mountable device. The skin-mountable device may take the form of or be similar in form to the eye-mountable device, and be configured to detect at least one analyte in a fluid (e.g., perspiration, blood, etc.) of a user wearing the skin-mountable device.

The sensor as described herein can include one or more conductive electrodes through which current can flow. Depending on the application, the electrodes can be configured for different purposes. For example, a sensor can include a working electrode, a reference electrode, and a counter-electrode. Also possible are two-electrode systems, in which the reference electrode serves as a counter-electrode. The working electrode can be connected to the reference electrode via a circuit, such as a potentiostat.

The electrode can be formed from any type of conductive material and can be patterned by any process that can be used for patterning such materials, such as deposition or photolithography, for example. The conductive materials can be, for example, gold, platinum, palladium, titanium, carbon, copper, silver/silver-chloride, conductors formed from noble materials, metals, or any combinations of these materials. Other materials can also be envisioned.

The crosslinked copolymer of the analyte sensor includes backbone chains of methacrylate-derived units, and an analyte sensing component, such as an enzyme, embedded within the copolymer. The first methacrylate-derived units of the backbone chains are each covalently bound to a side chain. Each of the second methacrylate-derived units is covalently bound through a linker to another second methacrylate-derived unit in a different backbone chain. The crosslinks, or groups through which the second methacrylate-derived units are connected to each other, are discussed in greater detail below. Various conformations and compositions of the side chains of the first methacrylate-derived units, and the crosslinks of the second methacrylate-derived units can be used to adjust the properties of the crosslinked copolymer as desired, which include permeability and the ability to immobilize an analyte sensing component.

The side chains of the first methacrylate-derived units can be water soluble or soluble in a water-miscible solvent, such as an alcohol. The side chains can have one or more heteroatoms, for example, nitrogen, oxygen or sulfur atoms. In some embodiments, the side chains have one or more hydroxy groups.

In some embodiments, the side chains include one or more alkylene oxide units. The alkylene oxide units can be derived from ethylene oxide, propylene oxide or butylene oxide, and can be a combination of two or three different alkylene oxide units. In some embodiments, the alkene oxide units form a poly(alkylene oxide) such as poly(ethylene glycol) or polypropylene glycol).

In some embodiments, the first methacrylate-derived units can have the structure of formula (I):

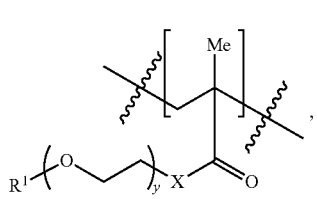

where X is —O—, —NR'— or —S—, y is 0, 1, 2, 3, 4, 5, 6, 7, 8, 9 or 10, and $R^1$ is hydrogen, —$C_1$-$C_{12}$alkyl, —$C_1$-$C_{12}$alkyl-OH, —$SiR'_3$, —C(O)—$C_1$-$C_{12}$alkyl, —$C_1$-$C_{12}$alkyl-C(O)OR', where R' is —$C_1$-$C_{12}$alkyl.

In certain embodiments, the first methacrylate-derived units have the structure:

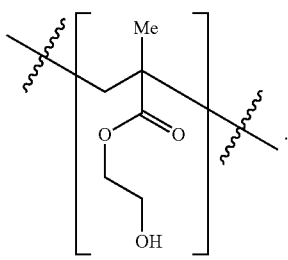

The crosslinks of the crosslinked copolymer connect the second methacrylate-derived units in different backbone chains, and are represented by "A" in formula (II):

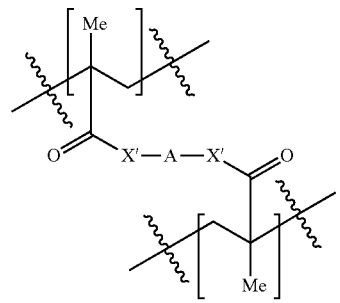

where X' is independently —O—, —NR'— or —S—, and A is a crosslink.

In some embodiments, the crosslinks can be soluble in water or a water-miscible solvent, such as an alcohol. The crosslinks can have one or more heteroatoms, for example, nitrogen, oxygen or sulfur atoms. In some embodiments, the crosslinks have one or more hydroxy groups.

In some embodiments, the crosslinks can include one or more alkylene oxide units. The alkylene oxide units can be in the form of a polymer, such as poly(ethylene glycol), poly(propylene glycol), poly(butylene oxide) or a mixture thereof, and can be a copolymer including a combination of two or three different alkylene oxide units. In some embodiments, the poly(alkylene oxide) of the crosslinks is a block copolymer including blocks of two or three different poly(alkylene oxide) polymers. In certain embodiments, the poly(alkylene oxide) is a block copolymer of poly(ethylene glycol) and poly(propylene glycol). In other embodiments, the crosslinks include poly(ethylene glycol).

In some embodiments, the crosslinks include one or more ethylene oxide units. For example, the crosslinks (e.g., A in formula II above) can have the structure of formula (IIa):

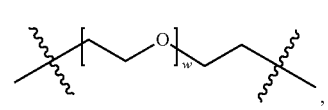

where w is 0, 1, 2, 3, 4, 5, 6, 7, 8, 9 or 10.

In certain embodiments, w is an average value of from about 2 to about 250.

In other embodiments, w in the crosslinks of formula (IIa) is such that the number average molecular weight ($M_n$) of the PEG portion (within the brackets in formula (IIa)) of the crosslinks is about 100 to about 10,000. For example, w can be selected such that the $M_n$ of the PEG portion of the crosslinks falls within a range in Table 1:

TABLE 1

| $M_n$ range of the PEG portion of the crosslinks (values are approximate). | |
|---|---|
| Low | High |
| 100 | 200 |
| 200 | 300 |
| 300 | 400 |
| 400 | 500 |
| 500 | 600 |
| 600 | 700 |
| 700 | 800 |

TABLE 1-continued $M_n$ range of the PEG portion of the crosslinks (values are approximate).

| Low | High |
|---|---|
| 800 | 900 |
| 900 | 1,000 |
| 1,000 | 2,000 |
| 2,000 | 3,000 |
| 3,000 | 4,000 |
| 4,000 | 5,000 |
| 5,000 | 6,000 |
| 7,000 | 8,000 |
| 8,000 | 9,000 |
| 9,000 | 10,000 |

In some embodiments, the crosslinks are derived from di(ethylene glycol) dimethacrylate, i.e., compounds of formula (II) or (IIa) where X' is independently —O—, —NR'— or —S—, and w is 1.

In some embodiments, the crosslinked copolymer of the analyte sensor can form a network having voids, which are regions within the copolymer that are not occupied by copolymer, and are referred to herein as "pores". The porous network of the crosslinked copolymer can facilitate control of the equilibrium between the concentration of the analyte (e.g., glucose) in the sample, and the analyte concentration in the proximity of the analyte sensor electrode surface. When all of the analyte arriving at the analyte sensor is consumed, the measured output signal can be linearly proportional to the flow of the analyte and thus to the concentration of the analyte. However, when the analyte consumption is limited by the kinetics of chemical or electrochemical activities in the analyte sensor, the measured output signal may no longer be controlled by the flow of analyte and may no longer be linearly proportional to the flow or concentration of the analyte. In this case, only a fraction of the analyte arriving at the analyte sensing component is consumed before the sensor becomes saturated, whereupon the measured signal stops increasing, or increases only slightly, with an increasing concentration of the analyte. The porous network can reduce the flow of the analyte to the analyte sensing component so the sensor does not become saturated and can therefore enable a wider range of analyte concentrations to be measured.

The properties of the porous network can be varied to produce desired properties, such as permeability of the analyte. For example, flow of the analyte into or across the sensor can be dependent on the specific analyte being monitored, and thus, the porous network can be altered to obtain properties for monitoring a specific analyte. As discussed in further detail below, in some applications, the porosity of the porous network can be modulated by adjusting the type and/or amount of porogen used when making the analyte sensor.

The analyte sensing component is embedded, i.e., surrounded by the copolymer network of the crosslinked copolymer. The embedded analyte sensing component is immobilized and can interact with a corresponding analyte of interest. In some embodiments, the analyte sensing component includes an enzyme.

The analyte sensing component of the analyte sensor can be selected to monitor physiological levels of a specific analyte. For example, glucose, lactate, cholesterol and various proteins and lipids can be found in body fluids, including, for example, tear film, and can be indicative of medical conditions that can benefit from continuous or semi-continuous monitoring.

The analyte sensing component can be an enzyme selected to monitor one or more analytes. For example, physiological cholesterol levels can be monitored with cholesterol oxidase, lactate levels with lactate oxidase, and glucose levels with glucose oxidase or glucose dehydrogenase (GDH).

In some embodiments, the analyte sensing component can be an enzyme that undergoes a chemical reaction with an analyte to produce detectable reaction products. For example, a copolymer including glucose oxidase ("GOx") can be situated around the working electrode to catalyze a reaction with glucose to produce hydrogen peroxide ($H_2O_2$). As shown below, the hydrogen peroxide can then be oxidized at the working electrode to releases electrons to the working electrode, which generates a current.

$$glucose + O_2 \xrightarrow{GOx} H_2O_2 + gluconolactone \quad H_2O_2 \rightarrow 2H^+ + O_2 + 2e^-$$

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportional to the concentration of the analyte molecules. The current can thus provide an indication of the analyte concentration.

In other embodiments, the analyte sensing component is glucose dehydrogenase (GDH). In certain instances, the use of GDH can require the addition of a cofactor such as flavin adenine dinucleotide (FAD), nicotinamide adenine dinucleotide (NAD), flavin mononucleotide, pyrroloquinoline quinone (PQQ) or a coenzyme.

The thickness of the crosslinked copolymer of the analyte sensor can vary depending on the desired properties of the analyte sensor. The thickness of the copolymer, as measured from the top of electrode to the top of the copolymer, can play an important role in regulating the flow of the analyte to the analyte sensing component. Depending on the characteristics of the methacrylate-derived units in the copolymer the type of analyte sensing component used, and the analyte to be monitored, the thickness of the copolymer can be from less than about 10 µm to about 30 µm. In some instances, the copolymer is less than 20 µm in thickness, where in other applications the copolymer is about 20 µm to about 25 µm in thickness. In certain applications, the copolymer is about 10 µm to about 15 µm in thickness, where in other applications the copolymer is about 15 µm to about 20 µm or about 25 µm to about 30 µm in thickness. In some embodiments, the copolymer is about 20 µm in thickness.

In another aspect, a method for making an analyte sensor is disclosed. The method can involve:
 a) forming a mixture comprising an analyte sensing component, one or more porogens, a dimethacrylate monomer, an initiator, and a methacrylate monomer having a side chain;
 b) depositing the mixture on a surface of an electrode; and
 c) curing the deposited mixture to form a cured copolymer.

In some implementations, the method can further involve removing the porogen from the cured copolymer.

The relative amounts of the components in the mixture can vary depending on the desired properties of the resulting analyte sensor. For example, adjusting the type and/or amount of porogen can alter the porous network of the crosslinked copolymer. Controlling the properties of the porous network can allow for the tuning of the permeability of the analyte sensor. Similar tunability can also be accomplished by adjusting the amount of mixture deposited on the electrode.

The mixture can be formed in an aqueous medium, alcoholic medium, or mixture thereof. The aqueous medium can include a buffered aqueous solution, such as, for example, a solution containing citric acid, acetic acid, borate, carbonate, bicarbonate, 4-2-hydroxyethyl-1-piperazineethanesulfonic acid (HEPES), 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 3-[N-Tris(hydroxymethyl)methylamino]-2-hydroxypropanesulfonic acid (TAPSO), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate), saline sodium citrate (SSC), 2-(N-morpholino)ethanesulfonic acid (MES), 2(R)-2-(methylamino)succinic acid, or phosphate buffered saline (PBS). In some embodiments, the mixture is formed in a mixture of a buffered aqueous solution and ethanol.

In some embodiments of the method, the percentage of each component can be varied in the mixture. In some instances, the percentage of analyte sensing component in the mixture, is about 20% by weight to about 50% by weight, the percentage of porogen is 1% by weight to about 30% by weight, and the percentage of first methacrylate monomer is about 30% by weight to about 60% by weight. All percentages are given as a percentage of the cumulative amount of analyte sensing component, porogen and first methacrylate monomer. In certain examples, the percentage of analyte sensing component is about 40%, the amount of porogen is about 10%, and the amount of first methacrylate monomer is about 50%. In certain embodiments, the mixture is thoroughly mixed, optionally with a stirrer or shaker, before being deposited onto a surface of an electrode.

In some embodiment of the method, the mixture can be formed by combining individual solutions containing the components of the mixture. For example, the method can involve:
a) forming a first solution including an analyte sensing component;
b) forming a second solution including one or more porogens;
c) forming a third solution including, a dimethacrylate monomer, an initiator, and a methacrylate monomer having a side chain;
d) combining the first, second, and third solutions to form the mixture.

In some embodiments of the method, the first, second and third solutions of the method are formed with approximately the same concentration of analyte sensing component, porogen, methacrylate monomer, respectively. The percentage of each component can then be varied by adjusting the amounts each solution used to form the mixture.

In some embodiments, the mixture can be formed on a surface of an electrode. For example, each component, or a combination of one or more components, can be individually deposited to form the mixture. Similarly, when the mixture is formed by combining individual solutions, the solutions can combined on a surface of an electrode to form the mixture.

The analyte sensing component can be selected based on the analyte desired to be monitored. For example, to monitor physiological cholesterol levels, cholesterol oxidase can be used, and to monitor lactate levels lactate oxidase can be used. To monitor glucose levels, the analyte sensing component can include glucose oxidase or glucose dehydrogenase (GDH).

The analyte sensing component can be present during polymerization of the methacrylate and dimethacrylate monomers in the deposited mixture, such that polymerization of the methacrylate and dimethacrylate monomers results in the formation of a crosslinked copolymer network in which the analyte sensing component is embedded. The embedded analyte sensing component is immobilized and can be used to monitor a corresponding analyte of interest.

The porogen is selected for properties that will allow for the removal of the porogen from the copolymer to form the pores of the copolymer network. The porogen can be water-soluble, nontoxic and biocompatible. The porogen can also have a structural size that enables the formation of pores that are not too small to let the analyte pass through, but not large enough to let the embedded analyte sensing component to leach out of the copolymer network. The range of porogen sizes can therefore be dependent on the analyte and/or the analyte sensing component used in the sensor. For example, when glucose concentration is monitored by a sensor having glucose oxidase, the average pore size can be large enough to allow for glucose (MW=180 D) permeability, but not too large to allow glucose oxidase (MW=160 kD) to leach out.

In some embodiments, the porogen is a salt, such as a water-soluble organic or inorganic salt. Organic salts can be Group 1 (e.g., Li, Na, K, Cs) or Group 2 (e.g., Mg, Ca, Sr, Ba) salts of carboxylic acids, such as monosodium glutamate. Also included are Group 1 or 2salts of carbonate $(CO_3)^{2-}$, bicarbonate $(HCO_3)^-$, and phosphate $(PO_4)^{3-}$. Inorganic salts include any combination of cations from the Group 1 or 2 elements with anions from the Group 17 elements (e.g., F, Cl, Br, I). In certain embodiments, the salt is NaCl.

In some embodiments, the porogen is a water-soluble polymer. Examples of water-soluble polymers include poly (alkylene oxide), poly(vinyl alcohol), polyacrylamide, sodium polyacrylate, lithium polyacrylate, potassium polyacrylate, ammonium polyacrylate and poly(N-vinyl pyrolidone). Poly(alkylene oxide) polymers that can be used as a porogen in the method include poly(ethylene glycol), poly (propylene glycol), poly(butylene oxide) or a mixture thereof. Alkylene oxide copolymers including a combination of two or three different alkylene oxide units can also be used as porogens in the method.

In certain embodiments, the porogen is poly(ethylene glycol) (PEG). In some examples the PEG has a number average molecular weight ($M_n$) of about 500 to about 10,000.

In some embodiments, the porogen is a sugar, which can be a monosaccharide, disaccharide, oligosaccharide, polysaccharide or amino sugar. Monosaccharides that can be used as a porogen in the method include glucose (dextrose), fructose (levulose), galactose, xylose and ribose. Monosaccharides can be used as porogens is their acyclic, pyranose or furanose forms, or a mixture thereof. Disaccharides include sucrose, lactose, and maltose, lactulose, trehalose and cellobiose. Oligosaccharides are saccharide polymers containing a small number (two to ten) of monosaccharide units. Polysaccharides are saccharide polymers containing a large number (ten or more) of monosaccharide units. Oligosaccharide and polysaccharide porogens as used in the method include water-soluble oligomers and water-soluble polymers of glucose, fructose, galactose, xylose or ribose. Amino sugar porogens include a sugar having a nitrogen atom, such as N-acetyl glucosamine, galactosamine, glucosamine, sialic acid and L-daunosamine.

Thus, in some embodiments, the porogen can be a salt, a water-soluble polymer, a sugar or any mixture thereof.

The first methacrylate monomer has side chains that can have one or more heteroatoms. In certain embodiments, the side chains are selected to form the crosslinked copolymer of the analyte sensor as described herein.

In some embodiments of the method, the methacrylate monomer has the structure of formula (III):

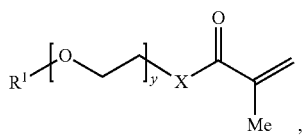
(III)

where X, y, $R^1$, and R' are selected to provide the first methacrylate-derived monomeric unit of the crosslinked copolymer described herein.

In certain embodiments of the method, the methacrylate monomer has the structure:

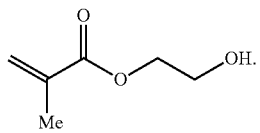

The dimethacrylate monomer is a molecule having two terminal methacrylate groups tethered by a linker. The linker is selected to provide the crosslinks between the second methacrylate-derived units in different backbone chains of the crosslinked copolymer described herein.

The extent of crosslinking in crosslinked copolymer of the analyte sensor can be controlled by adjusting the amount of dimethacrylate monomer in the mixture. In some embodiments, the dimethacrylate monomer is about 0.1% to about 15% of the mixture. In other examples, the amount is about 1% to about 5%, or about 5% to about 10%, or about 10% to about 15% of the mixture. In some embodiments, the amount is about 1%. In some instances, the mixture includes about 1% of the dimethacrylate monomer.

In some embodiments of the method, the dimethacrylate monomer includes one or more alkylene oxide units to provide the crosslinks of the crosslinked copolymer described herein. In some embodiments, the dimethacrylate monomer includes poly(ethylene glycol) (PEG). For example, the dimethacrylate monomer can have the structure of formula (IV):

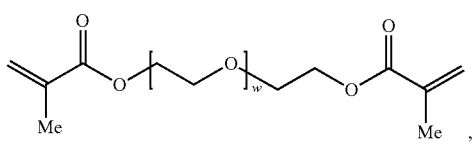
(IV)

where w is 0, 1, 2, 3, 4, 5, 6, 7, 8, 9 or 10.

In other embodiments of the method, the dimethacrylate monomer can have the structure of formula (IV) where w is such that the number average molecular weight ($M_n$) of the PEG portion of the dimethacrylate monomer is about 100 to about 10,000. For example, w can be selected such that the $M_n$ of the PEG portion of dimethacrylate monomer falls within a range in Table 1. In some embodiments, the dimethacrylate monomer is di(ethylene glycol) dimethacrylate.

Depositing the mixture onto a surface of an electrode can be accomplished by a number of methods. For example, the depositing can be performed manually with a micro-syringe, or by automated fabrication processes with nano jet dispensing equipment.

In some embodiments of the method, the amount of mixture deposited onto a surface of an electrode is selected to provide the desired thickness of the crosslinked copolymer of the analyte sensor. In some examples, the amount deposited on the electrode is about 50 nL/mm$^2$ to about 500 nL/mm$^2$. In some examples, the amount is about 50 nL/mm$^2$ to about 150 nL/mm$^2$, or about 150 nL/mm$^2$ to about 300 nL/mm$^2$, or about 300 nL/mm$^2$ to about 500 nL/mm$^2$. In some embodiments, the amount is about 100 nL/mm$^2$. In a specific example, about 100 nL/mm$^2$ of the mixture is deposited on the electrode and cured to provide a crosslinked copolymer that is about 20 μm in thickness.

Conditions suitable to initiate polymerization (i.e., curing) can be selected based on the characteristics of the initiator and the monomers being polymerized, but not to degrade the analyte sensing component. In embodiments where the analyte sensing component is an enzyme, the temperature and pH of the method can be selected to preserve the activity of the enzyme. In certain embodiments the initiator is activated with ultraviolet (UV) light. For example, when 2,2-dimethoxy-2-phenylacetophenone is used as an initiator, the curing can be performed with UV light.

After the crosslinked copolymer is formed, the porogen can be removed, for example, by washing the cured copolymer with an aqueous solution. The properties of the aqueous solution can be selected based on the porogen used in the method. In some examples, the aqueous solution is water or buffered water (e.g., PBS). In other instances, the porogen is removed with an acidic (pH<7) solution or a basic (pH>7) solution. In some embodiments, the aqueous solution includes an alcohol, such as ethanol. In other embodiments, the aqueous solution includes a water miscible organic solvent, such as tetrahydrofuran (THF).

EXAMPLES

Example 1

Immobilization of GOx in a Porous, Crosslinked Methacrylate Copolymer

Three solutions (A-C) were prepared:
A) 25 mg/ml glucose oxidase (GOx) in PBS buffer (pH=7.4)
B) 100 mg/ml poly(ethylene glycol) (average Mn 2,000, Aldrich product #81221) in PBS buffer (pH=7.4)
C) 2-hydroxyethyl methacrylate monomer solution containing 1% by weight di(ethylene glycol) dimethacrylate and 1% by weight 2,2-dimethoxy-2-phenylacetophenone.

A volume of each of the three solutions (A-C) was according to the ratios in the following table:

| A | B | C |
|---|---|---|
| 0.40 | 0.10 | 0.50 |

The resulting formulations were thoroughly mixed with a vortex shaker. A micro-syringe was used to deposit 100 nL/mm² of each formulation onto a sensor electrode, and the deposited formulation was UV-cured for 5 minutes at 365 nm under nitrogen with an EC-500 light exposure chamber (Electro-Lite Corp). The resulting cured, crosslinked copolymer had a thickness of about 20 μm.

Example 2

Analyte Sensor Performance in a Glucose Solution

The analyte sensor formed in Example 1 was tested at concentrations of glucose in phosphate buffered saline (PBS) ranging from 100 μM to 1,200 μM. The sensor was submerged in PBS and the glucose concentration was increased every 2-7 minutes. The current generated at the electrode was measured using a potentiostat (See FIG. 1). A linear relationship between current and glucose concentration was observed (See inset, FIG. 1).

Although the crosslinked polymer networks in the above examples comprise methacrylate groups, there are a number of ethylenically unsaturated groups known in the art to be capable of undergoing polymerization. Ethylenically unsaturated monomers and macromers may be either acrylic- or vinyl-containing monomers contain the vinyl grouping ($CH_2=CH-$), and are generally highly reactive. Acrylic-containing monomers are represented by the formula:

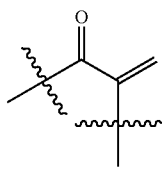 [SMILES: *C(=C)C(*)=O]

Examples of suitable polymerizable groups may include acrylic-, ethacrylic-, itaconic-, styryl-, acrylamido-, methacrylamido- and vinyl-containing groups such as the allyl group.

In addition to the above disclosed methods of forming crosslinked polymer networks by the polymerization of ethylenically unsaturated monomers and macromonomers, additional chemistries will be known to one or ordinary skill in the art to from such networks. As an example, epoxy chemistry, in which multifunctional amines and multifunctional epoxy compounds are mixed together and cured, can be used to form cross-linked polymer networks. Additionally, urethane chemistry may be used, in which multifunctional isocyanates are mixed with multifunctional alcohols and cured to provide cross-linked polymer networks. Other chemistries for the formation of cross-linked polymer networks exist, and will be well known to those of ordinary skill in the art.

It should be understood that arrangements described herein are for purposes of example only. As such, those skilled in the art will appreciate that other arrangements and other elements (e.g., machines, interfaces, functions, orders, and groupings of functions, etc.) can be used instead, and some elements can be omitted altogether according to the desired results. Further, many of the elements that are described are functional entities that can be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

The invention claimed is:

1. An analyte sensor comprising:
a crosslinked copolymer network in contact with a surface of an electrode, wherein the crosslinked copolymer network consists of:
backbone chains comprising first methacrylate-derived units and second methacrylate-derived units, wherein each first methacrylate-derived unit has a side chain; and
crosslinks between the second methacrylate-derived units in different backbone chains, wherein the crosslinks comprise poly(alkylene oxide);
an analyte sensing component embedded within the crosslinked copolymer network; and
voids within and defined by the crosslinked copolymer network, wherein the voids are large enough to allow an analyte to pass through the crosslinked copolymer network and small enough to not allow the analyte sensing component to pass through the crosslinked copolymer network.

2. The sensor according to claim 1, wherein the side chain of the first methacrylate-derived units comprise one or more hydroxy groups.

3. The sensor according to claim 1, wherein the first methacrylate-derived units have the structure of formula (I):

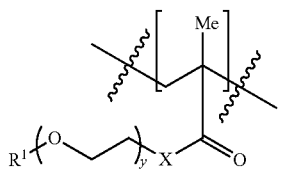

(I)

wherein
X is —O—, —NR'— or —S—;
y is 0-10; and
R¹ is hydrogen, —$C_1$-$C_{12}$alkyl, —$C_1$-$C_{12}$alkyl-OH, —SiR'$_3$, —C(O)—$C_1$-$C_{12}$alkyl, —$C_1$-$C_{12}$alkyl-C(O)OR', wherein R' is —$C_1$-$C_{12}$alkyl.

4. The sensor according to claim 1, wherein the first methacrylate-derived units have the structure:

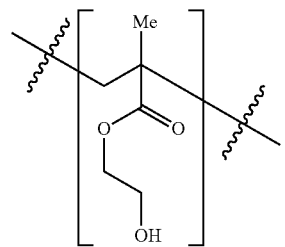

5. The sensor according to claim 1, wherein the crosslinks have the structure of formula (IIa):

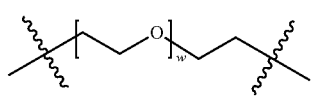

(IIa)

wherein w is 2-10.

6. The sensor according to claim 1, wherein the crosslinks have the structure of formula (IIa):

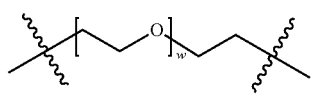

(IIa)

wherein w is an average value of from about 2 to about 250.

7. The sensor according to claim 1, wherein the crosslinks are derived from the di(ethylene glycol) portion of di(ethylene glycol) dimethacrylate.

8. The sensor according to claim 1, wherein the analyte sensing component comprises glucose oxidase.

9. The sensor according to claim 1, wherein the crosslinked copolymer network has a thickness of about 10 µm to about 30 µm.

10. The sensor according to claim 1, wherein the first methacrylate-derived units have the structure of formula (I):

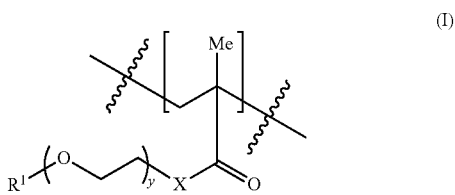

(I)

wherein
X is —O—, —NR'— or —S—;
y is 0-10; and
R¹ is hydrogen, —$C_1$-$C_{12}$alkyl, —$C_1$-$C_{12}$alkyl-OH, —SiR'$_3$, —C(O)—$C_1$-$C_{12}$alkyl, —$C_1$-$C_{12}$alkyl-C(O)OR', wherein R' is —$C_1$-$C_{12}$alkyl;
the crosslinks have the structure of formula (IIa):

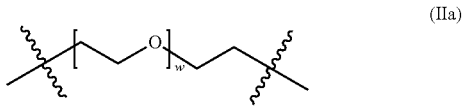

(IIa)

wherein w is 2-10; and
the analyte sensing component comprises glucose oxidase.

11. The sensor of claim 8, wherein the analyte is glucose and the voids within and defined by the crosslinked copolymer network are large enough to allow glucose to pass through the crosslinked copolymer network and small enough to not allow glucose oxidase to pass through the crosslinked copolymer network.

* * * * *